United States Patent
Wu et al.

(10) Patent No.: US 6,630,595 B2
(45) Date of Patent: Oct. 7, 2003

(54) METHOD FOR PRODUCING MALEIMIDES

(75) Inventors: Kuo-Ching Wu, Hsinchu (TW);
Yu-Lan Tung, Hsinchu (TW);
Chiou-Hwang Lee, Hsinchu (TW);
Jyh-Chang Dai, Hsinchu Hsien (TW);
Chiung-Hui Huang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 15 days.

(21) Appl. No.: 10/160,159

(22) Filed: Jun. 4, 2002

(65) Prior Publication Data
US 2003/0105337 A1 Jun. 5, 2003

(30) Foreign Application Priority Data

Dec. 4, 2001 (TW) .................................... 90129962 A

(51) Int. Cl.$^7$ ............................................ C07D 207/18
(52) U.S. Cl. ........................................ 548/548
(58) Field of Search .......................... 548/548

(56) References Cited

U.S. PATENT DOCUMENTS

| 4,812,579 A | * | 3/1989 | Doi et al. ................... 548/548 |
| 4,980,483 A | * | 12/1990 | Kita et al. .................. 548/548 |
| 5,741,913 A | * | 4/1998 | Oda et al. ................... 548/548 |

* cited by examiner

*Primary Examiner*—Joseph K. McKane
*Assistant Examiner*—Golam M. M. Shameem
(74) *Attorney, Agent, or Firm*—Sughrue Mion, PLLC

(57) ABSTRACT

A method for producing maleimides. The method comprises reacting maleic anhydride and a primary amine at 100–180° C. in an organic solvent using a solid acidic catalyst, and purifying the maleimide produced therefrom by extraction and crystallization. The molar ratio of the primary amine to maleic anhydride is about 0.8–1.6. With the present invention, high production yield with high purity of maleimides can be achieved. In addition, the solid acidic catalyst can be easily separated and recycled for subsequent use. Thus, the present invention provides a number of distinct advantages, including substantially improved yield, conveniently reusable catalyst, reduced waste disposal and lower costs.

11 Claims, No Drawings

METHOD FOR PRODUCING MALEIMIDES

BACKGROUND OF THE INVENTION

1. Field of the Invention

The present invention generally relates to a novel method for the preparation of maleimides. More specifically, the present invention relates to a method involving direct imidation of maleic anhydride and a primary amine to afford maleimides.

2. Description of the Related Art

Maleimides and their derivatives are widely used in various industrial fields, such as synthetic resins, medicine, agricultural chemistry, and heat-resistant polymer modifiers or photo-electrical materials.

A typical method for preparing maleimides uses direct amination of maleic anhydride and a primary amine to produce maleamic acid intermediate, followed by dehydrated cyclization (imidation) with a dehydrating agent (e.g., acetic anhydride). By this method, however, each mole of maleimide needs one mole of acetic anhydride and produces two moles of acetic acid, which causes corrosion in the equipment and result in complex follow-up treatments and environmental pollution. Such method has been disclosed in U.S. Pat. No. 2,444,536, in which acetic anhydride and sodium acetate are used as catalysts.

Another method disclosed in UK Patent No. 1,041,027 and U.S. Pat. No. 3,431,276 utilizes an acidic catalyst and an organic solvent with a boiling point higher than 80° C. in an azeotropic distillation system for preparing maleimides, wherein water produced is constantly removed. The organic solvent can be toluene, xylene, or chlorobenzene, and the catalyst can be sulfur trioxide, sulfuric acid or phosphoric acid. Although this method requires a lesser amount of the expensive dehydrating agent, the production yield is not satisfactory, thus rendering the process uneconomical.

Furthermore, it is disclosed in Japanese Patent Publication No. 53-68700 and Japanese Patent Publication No. 57-42043 that adding an aprotic polar solvent can improve the solubility of the maleamic acid intermediate, and consequently results in a higher yield. However, aprotic polar solvent is highly poisonous and difficult to remove because of its high boiling point.

Japanese Patent No. 54-30155 discloses a high yield method using quaternary amine salts of organic or inorganic acids as catalysts to synthesize oligmers of maleimide. In this method, a certain ratio of quaternary amine salts/acids must be maintained to exhibit satisfactory activity, but such ratio varies in recycled catalysts, and therefore the recycled catalysts must be purified and modified to attain the required ratio. This adds further complexity to the process and results in higher production costs.

In addition, Japanese Patent Publication No. 60-109562 discloses a method using a solvent containing a certain ratio of non-polar solvent and polar solvent, and amino salts of p-benzosulfonic or o-benzosulfonic acid as catalyst, wherein the polar solvent improves the solubility of maleamic acid and catalyst to boost the production yield. However, the polar solvent makes the product, catalyst and solvent in the same phase, thereby increasing the cost of purifying the product.

Furthermore, a small amount of gel byproduct (oligmers) will be produced during the maleimide reaction, which is soluble in reaction solution, but precipitates out when the solution is cooled to below 80° C. In this case, the gel byproduct remains in the catalyst, and affects the activity of the catalyst. Although Japan Publication No. 5-213869 discloses that water can be used to recycle carriers; a new catalyst must be added to compromise those lost during recycling. This again further adds complexity to the process, making the process uneconomical.

SUMMARY OF THE INVENTION

Therefore, an object of the present invention is to provide a method for producing maleimides using solid acidic catalyst instead of liquid acid catalyst or liquid acid catalyst mixed with solid carriers. According to the invention, maleic anhydride and a primary amine are reacted in the presence of organic solvent to produce maleimide on a solid acidic catalyst. The reaction temperature is preferably between about 100 and 180° C., and the molar ratio of maleic anhydride/primary amine is preferably 0.6~1.8. After the reaction is completed, the catalyst is separated and removed from the solvent to obtain crude maleimide. Then, a high purity maleimide can be obtained by a two-step extraction and crystallization.

The above and other objects are achieved by reacting maleic anhydride and a primary amine at about 100–180° C. in an organic solvent and in the presence of a solid acidic catalyst, wherein the molar ratio of the primary amine to the maleic anhydride is about 0.8–1.6.

The primary amine can be straight chain, branched, cyclic, or aromatic amines containing 1–8 carbon atoms. Preferred organic solvents include but are not limited to toluene and xylene.

The method of the invention may further comprise: (I) extracting and crystallizing with an organic solvent having a polarity of less than 0.05; and (II) extracting and crystallizing with an organic solvent having a polarity of greater than 0.2. The organic solvent having a polarity of less than 0.05 is n-hexane or n-pentane, and the organic solvent having a polarity of greater than 0.2 is toluene or xylene.

The solid acidic catalyst is preferably an inorganic acid supported in a neutral carrier such as silicon oxide, zirconium oxide, diatomite or silica gel, and the Hammett Index of the neutral carrier should be greater than −2. The inorganic acid can be sulfuric acid or phosphoric acid. The solid acidic catalyst is preferably prepared by roasting at about 200~400° C. The preferable amount of the catalyst is about 50~200 wt % relative to maleamic acid.

The maleimide reaction is carried out in a low-polarity organic solvent having a boiling point between about 100 and 250° C. Upon the completion of the reaction, the solid acidic catalyst and the reaction mixture are filtered at the reaction temperature or below the reaction temperature. The solid acidic catalyst is then set aside for recycling, and the crude maleimide is obtained by evaporation of the solvent. Next, by distilling the crude maleimide under reduced pressure, a high purity maleimide can be afforded.

However, since maleimide is not thermally stable, it deteriorates easily when distilled. To overcome this problem, the present invention features two-step extraction and crystallization to purify crude maleimide. The two steps include: (I) using an organic solvent with a polarity of less than 0.05 as the extractant; and (II) using an organic solvent with a polarity of greater than 0.2 as the extractant. The maleimide thus purified reaches a purity of greater than 99.5 wt %. The organic solvent with a polarity of less than 0.05 is, for example, n-hexane or n-pentane; and the organic solvent with a polarity of greater than 0.2 is, for example, toluene or xylene.

One important advantage of the invention is that this method is applicable in both batch or continuous reactors to attain high yield. In addition, the separation of product and catalyst is much easier. This is because the solid acid catalyst and the solution exist in different phases (solid phase vs. liquid phase) during the reaction. Accordingly, the catalyst and the solution can be separated at various temperatures, and the recycled solid acidic catalyst still exhibits good activity and selectivity. Furthermore, it is viable to separate the catalyst from the solution after cooling the reaction mixture to room temperature. In other words, either at room temperature or reaction temperature, the catalyst can be easily and fully separated for recycle.

In addition, according to the method of the present invention, the gel byproducts produced when cooling the reaction solution to room temperature will segregate out and be separated from the reaction solution automatically. Therefore, there is no byproduct deposit on the catalyst surface, thus avoiding the above-mentioned problem of catalysts losing activity when recycled.

DETAILED DESCRIPTION OF THE PREFERRED EMBODIMENTS

Reference is now made in detail to embodiments of the present invention that illustrate the best mode presently contemplated by the inventor(s) for practicing the present invention.

EXAMPLE 1

80 g of zirconium dioxide was kneaded in a kneading machine. After addition of 50 ml of 85% p-phosphoric acid, the kneading was continued for a further 30 minutes. Thereafter, the catalyst was roasted at 300° C. for 6 hours to give the desired solid acidic catalyst.

200 ml of xylene was placed in a three-neck reactor, followed by addition of 10 g of maleic anhydride. The mixture was stirred to dissolve completely, and then 15 ml of cyclohexyl amine was slowly added into the mixture. After completion of the addition, the mixture was stirred for a further 30 minutes. Then 20 g of the solid acidic catalyst was added and the reaction mixture was heated to 144° C. for 8 hours. The reaction solution was analyzed by liquid chromatography, and the yield of N-cyclohexyl maleimide was 93.67 mol % (based on maleic anhydride).

The reaction solution and catalyst were separated by filtration directly at 144° C. The catalyst was set aside for the next experiment, and the reaction solution was cooled to room temperature. Evaporation of the solvent furnished 16.5 g of N-cyclohexyl maleimide as light yellow solid. The purity was 98.70%.

EXAMPLE 2

200 ml of xylene was placed in a 500 ml three-neck reactor, followed by addition of 10 g of maleic anhydride. The mixture was stirred to dissolve completely, and then 11.5 ml of cyclohexyl amine was slowly added into the mixture. After completion of the addition, the mixture was stirred for a further 30 minutes. Then 20 g of the solid acidic catalyst recycled from Example 1 was added and the reaction mixture was heated to 144° C. for 8 hours. The solution obtained was analyzed by liquid chromatography, and the yield of N-cyclohexyl maleimide was 95.85 mol % (based on maleic anhydride).

EXAMPLE 3~12

The same procedure as described in Example 2 was repeated (using the recycled solid acidic catalyst repeatedly), and yields of every product obtained are summarized in Table 1.

TABLE 1

| Ex. | 3 | 4 | 5 | 6 | 7 | 8 | 9 | 10 | 11 | 12 |
|---|---|---|---|---|---|---|---|---|---|---|
| Yield (mol %) | 97.06 | 98.16 | 95.85 | 95.37 | 93.03 | 95.89 | 93.45 | 95.75 | 93.03 | 96.52 |

As shown in Table 1, the solid acidic catalyst was used several times without deteriorating the product yield, which remained above 93%. It is evident that the method for producing maleimide according to the present invention can maintain the activity of the solid acidic catalyst.

EXAMPLE 13

The catalyst recycled in Example 12 was used in this example. 200 ml of xylene was placed in a 500 ml three-neck reactor, followed by addition of 20 g of cyclohexyl maleamic acid. The mixture was heated and stirred to dissolve completely. The recycled catalyst was then added and the mixture was heated to 144° C. for 8 hours. The reaction solution was analyzed by liquid chromatography, and the yield of N-cyclohexyl maleimide was 96.89 mol % (based on maleic anhydride).

In this Example, even though using the maleamic acid intermediate as raw material, the production yield was as high as 96.89 mol % by the method of the present invention.

COMPARATIVE EXAMPLE 1

50 ml of 85% p-phosphoric acid was added into 80 g of silicon dioxide to make a solid acid catalyst.

200 ml of xylene was placed in a 500 ml three-neck reactor, followed by addition of 10 g of maleic anhydride. The mixture was stirred to dissolve completely, and then 15 ml of cyclohexyl amine was slowly added into the mixture. After completion of the addition, the mixture was stirred for a further 30 minutes. Then 20 g of the above solid acidic catalyst was added and the reaction mixture was heated to 144° C. for 8 hours. The reaction solution was analyzed by liquid chromatography, and the yield of N-cyclohexyl maleimide was 89.97 mol % (based on maleic anhydride).

COMPARATIVE EXAMPLE 2

200 ml of xylene was placed in a 500 ml three-neck reactor, followed by the addition of 10 g of maleic anhydride. The mixture was stirred to dissolve completely, and then 11.5 ml of cyclohexyl amine was slowly added into the mixture. After completion of the addition, the mixture was stirred for a further 30 minutes. Then 20 g of the solid acidic catalyst recycled from Comparative Example 1 was added and the reaction mixture was heated to 144° C. for 8 hours. The reaction solution was analyzed by liquid chromatography, and the yield of N-cyclohexyl maleimide was 43.73 mol % (based on maleic anhydride).

From the two comparative examples, it was observed that using non-roasted solid acidic catalyst for the second time reduced the production yield to 43.73 mol %. Accordingly, roasting at high temperature is necessary to maintain the activity of solid acidic catalyst at a satisfactory level.

EXAMPLE 14

600 g of silicon dioxide was kneaded in a kneading machine. After addition of 375 ml of 85% p-phosphoric acid, the kneading was continued for a further 30 minutes. Thereafter, the catalyst was roasted at 300° C. for 4 hours to give the desired solid acidic catalyst.

6 L of xylene was placed in a three-neck reactor, followed by addition of 300 g of maleic anhydride. The mixture was stirred to dissolve completely, and then 353 ml of cyclohexyl amine was slowly added into the mixture. After completion of the addition, the mixture was stirred for a further 30 minutes. Then 600 g of the solid acidic catalyst was added and the reaction mixture was heated to 144° C. for 8 hours. The reaction solution was analyzed by liquid chromatography, and the yield of N-cyclohexyl maleimide was 95.58 mol % (based on maleic anhydride).

The reaction solution and catalyst were separated by filtration directly at 144° C. The catalyst was set aside, and the reaction solution was cooled to room temperature. Evaporation of the solvent furnished 520 g of crude N-cyclohexyl maleimide as yellow solid. The purity was 98.53%.

The crude N-cyclohexyl maleimide was extracted with 1 L of 10° C. n-hexane and re-crystallized at −10° C. The extraction and crystallization were repeated to afford 503 g of N-cyclohexyl maleimide, which was further crystallized using toluene to obtain transparent N-cyclohexyl maleimide as final product. The purity was 99.68%.

Accordingly, by the extraction and crystallization techniques of the present invention, maleimide with purity greater than 99% is obtainable.

EXAMPLE 15

40 g of zirconium dioxide was kneaded in a kneading machine. After addition of 20 ml of sulfuric acid, the kneading was continued for a further 30 minutes. Thereafter, the catalyst was roasted at 500° C. for 4 hours to give the desired solid acidic catalyst.

200 ml of toluene was placed in a three-neck reactor, followed by addition of 10 g of maleic anhydride. The mixture was stirred to dissolve completely, and then 14 ml of n-butyl amine was slowly added into the mixture. After completion of the addition, the mixture was stirred for a further 30 minutes. Then 20 g of the solid acidic catalyst was added and the reaction mixture was heated to 144° C. for 4 hours. The reaction solution obtained was analyzed by liquid chromatography, and the yield of N-cyclohexyl maleimide was 95.75 mol % (based on maleic anhydride).

The solution and catalyst were separated by filtration directly at 144° C. The catalyst was set aside and the solution was cooled to room temperature.

EXAMPLE 16

200 ml of toluene was placed in a 500 ml three-neck reactor, followed by addition of 10 g of maleic anhydride. The mixture was stirred to dissolve completely, and then 14 ml of n-butyl amine was slowly added into the mixture. After completion of the addition, the mixture was stirred for a further 30 minutes. Then 20 g of the solid acidic catalyst recycled from Example 15 was added and the reaction mixture was heated to 112° C. for 8 hours. The reaction solution was analyzed by liquid chromatography, and the yield of N-cyclohexyl maleimide was 95.60 mol % (based on maleic anhydride).

Examples 15 and 16 illustrate that the result obtained by using zirconium dioxide as neutral carrier of the solid acidic catalyst is as good as other Examples.

From the results shown above, the production yield according to the present method for making maleimides is higher than 95%. The catalyst still works well after 10 times of reactions without deterioration. Moreover, the catalyst is not as viscous as phosphoric amine salts and, can be easily separated at high temperature or room temperature by filtration. Consequently, deterioration of catalyst due to distillation at high temperature can be avoided.

According to the method of the present invention, high yield with high purity of maleimides can be obtained with lower production costs. Therefore, a much more economical method as compared to prior art methods is accomplished.

While the invention has been described by way of example and in terms of the preferred embodiment, it is to be understood that the invention is not limited to the disclosed embodiments. On the contrary, it is intended to cover various modifications and similar arrangements as would be apparent to those skilled in the art. Similarly, any process steps described herein may be interchangeable with other steps in order to achieve the same result. Therefore, the scope of the appended claims should be accorded the broadest interpretation so as to encompass all such modifications and similar arrangements, which is defined by the following claims and their equivalents.

What is claimed is:

1. A method for producing a maleimide, comprising reacting maleic anhydride and a primary amine at about 100–180° C. in an organic solvent and in the presence of a solid acidic catalyst which is prepared by roasting at about 200–400° C., wherein the molar ratio of the primary amine to maleic anhydride is about 0.8–1.6.

2. The method as claimed in claim 1, further comprising purifying the maleimide by extraction and crystallization.

3. The method as claimed in claim 1, wherein the primary amine is a straight chain, branched, cyclic, or aromatic amine containing 1–8 carbon atoms.

4. The method as claimed in claim 1, wherein the organic solvent is toluene or xylene.

5. The method as claimed in claim 1, wherein the solid acidic catalyst is an inorganic acid supported in a neutral carrier.

6. The method as claimed in claim 5, wherein the Hammett Index of the neutral carrier is greater than −2.

7. The method as claimed in claim 5, wherein the inorganic acid is sulfuric acid or phosphoric acid.

8. The method as claimed in claim 5, wherein the neutral carrier is silicon oxide, zirconium oxide, diatomite or silica gel.

9. The method as claimed in claim 2, wherein the extraction and crystallization are first carried out with an organic solvent having a polarity of less than 0.05, and then with an organic solvent having a polarity of greater than 0.2.

10. The method as claimed in claim 9, wherein the organic solvent having a polarity of less than 0.05 is n-hexane or n-pentane.

11. The method as claimed in claim 9, wherein the organic solvent having a polarity of greater than 0.2 is toluene or o-xylene.

* * * * *